United States Patent [19]

Micetich et al.

[11] 4,057,540

[45] Nov. 8, 1977

[54] 4-CHLOROAZETIDINONE-1-(2',3'-DICHLOROISOPROPYL) ACETATES AND PROCESS FOR PREPARING SAME

[75] Inventors: Ronald G. Micetich, Edmonton, Canada; Robert B. Morin, Warren, N.J.; Kenneth E. Wilson, Edmonton, Canada

[73] Assignee: Connlab Holdings Limited, Ontario, Canada

[21] Appl. No.: 667,825

[22] Filed: Mar. 17, 1976

[30] Foreign Application Priority Data

Apr. 22, 1975 United Kingdom ............... 16582/75

[51] Int. Cl.² .................. C07D 205/08; C07D 513/04; C07D 417/12
[52] U.S. Cl. ............................ 260/239 A; 260/308 D; 260/326 E; 260/326 N; 260/332.2 H; 260/306.5; 424/244; 544/5; 544/15; 544/27; 544/29; 544/30; 544/28
[58] Field of Search ........ 260/239 A, 308 D, 332.2 H

[56] References Cited

U.S. PATENT DOCUMENTS 3,962,276  6/1976  Kukolja .......................... 260/239 A Primary Examiner—Paul M. Coughlan, Jr.
Assistant Examiner—Mark L. Berch
Attorney, Agent, or Firm—Cushman, Darby & Cushman

[57] ABSTRACT

The invention relates to novel azetidinones of the general formula:

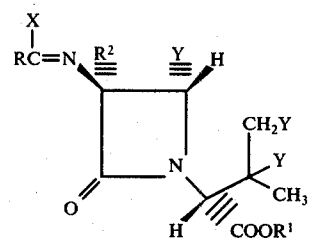

wherein R stands for lower alkyl, phenyl, phenyloxyloweralkyl, phenylloweralkyl, 2-thiophenemethyl, 5-tetrazolylmethyl, $R^3O-$ and $R^3S-$, wherein $R^3$ stands for lower alkyl, phenyl or phenylloweralkyl; $R^1$ is hydrogen or a cleavable radical selected from lower alkyl; loweralkoxymethyl, 2,2,2-trichloroethyl, benzyl, p-halobenzyl, p-nitrobenzyl and p-methoxybenzyl, benzhydryl and trimethylsilyl; $R^2$ is hydrogen or methoxy; X is SCl, SBr or —OH in which case the $C_3$-sidechain is better represented as the amide RCONH— group; Y is chloro or bromo; and

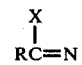

may also be taken as phthalimido.

These novel compounds possess antibacterial activity and are useful intermediates for the synthesis of modified penicillins and the analogues of penicillins.

5 Claims, No Drawings

4-CHLOROAZETIDINONE-1-(2',3'-DICHLOROISOPROPYL) ACETATES AND PROCESS FOR PREPARING SAME

The present invention relates to a novel process for the preparation of new azetidinone derivatives which have antibacterial activity and are useful intermediates for the synthesis of modified penicillins and the analogues of cephalosporins and penicillins in which the sulfur is replaced by oxygen and nitrogen (examples being the so-called oxacephalosporins and azacephalosporins).

PRIOR ART

Penicillins, 1 (Flowsheet 1), penicillin sulfoxides, 6, and anhydropenicillins, 4, particularly the 6-phthalimido compounds

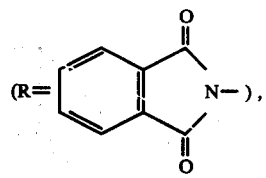

undergo an electrophilic ring opening with chlorine, sulfuryl chloride, and 1-chlorobenzothiazole (in the case of the penicillins, 1), in a suitable solvent such as carbon tetrachloride or methylene chloride to give the products indicated in Flowsheet 1. In the case of the pencillins, 1, the initial product, the 4-chloroazetidinone sulfenyl compounds, 2, formed with one equivalent of chlorine or sulfuryl chloride, rapidly converts to a cis-trans mixture of the 4-chloroazetidinone-1-iso-propylidene compounds, 3, with triethylamine or with excess of the chlorinating agent. Two problems associated with these reactions are the formation of both the cis and trans-isomers in the reactions from penicillins and anhydropenicillins, and the fact that the reactions work well with the phthalimido compounds, but not as cleanly with the commercially available penicillins (penicillin V and penicillin G).

The penicillin sulfoxides, 6, on heating in the presence of thionyl chloride are converted to the 3-chlorocephams, 10, and the 2-chloromethylpenams, 11, via the azetidinonethiriranium chlorides, 9, and the azetidinone-4-sulfenyl chlorides, 8. [S. Kukolja et. al., *J. Amer. Chem. Soc.*, 94, 7169 (1972)]. With sulfuryl chloride, the product is a mixture of the azetidinone-4-sulfinyl chlorides, 7, epimeric at sulfur, which with triethylamine form the 3-cephem sulfoxide. [S. Kukolja et. al., *Angew. Chem. Int.*, 12, 67 (1973)].

The products from these reactions have been converted to pencillins, 5-epipenicillins, 2-thiocephams, and by multistage processes to 1-oxapenams, 1-azacephalosporins, and 1-oxacephalosporins. The 1-oxa, 1-aza, and 1-methylenecephalosporins have also been made recently by a total (multistep) synthetic procedure and have been found to be bioactive [Ger. Offen. 2,355,209, Nov. 5, 1973].

Sheehan and co-workers [*J. Amer. Chem. Soc.*, 95, 3064 (1973)], found that the azetidione-4-sulfides 12a and 12b (Flowsheet 2) when reacted with chlorine in carbon tetrachloride underwent cleavage on either side of the sulfide bond (depending on the structure) to give the 4-chloroazetidinone, 13 or the azetidinone-4-sulfenylchloride, 14 respectively, the azetidinone-4-sulfenyl chloride, 14, being moderately stable.

Penicillin sulfoxides, 15 (Flowsheet 3) on heating generate the respective reactive sulfenic acids, which may be trapped by mercaptans to form unsym-azetidinone disulfides, 16. When the 6-thioamids or 6-thiocarbamates of penicillin sulfoxides, 15 (RCONH = RCSNH) are heated, the sulfenic acids produced undergo an intramolecular trapping reaction to form the 1,2,4-dithiazineazetidinones, 17. The unsym-azetidinone disulfides, 16, under controlled conditions in solvents such as carbon tetrachloride, chloroform, or methylene chloride, react with chlorine, bromine, or sulfuryl chloride, to give excellent yields of the 3-halocephams, 23, and/or the 2-halomethylpenams, 24, via the azetidinonethiiranium halide intermediates 22. [T. Kamiya et. al., Abstracts of the 4th International Congress of Heterocyclic Chemistry at Salt Lake City, Utah (1972) p. 97, and *Tetrahedron Letters*, 3001 (1973)].

THE INVENTION

In accordance with the present invention there is now provided novel 4-chloro or bromoazetidinone-1-(2',3'-dichloro or dibromoisopropyl)acetates, of the general formula, 18:

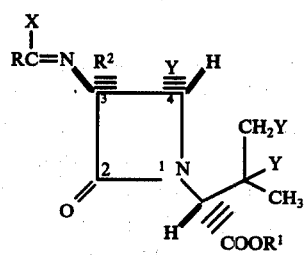

wherein:
R stands for lower alkyl, phenyl, phenyloxyloweralkyl, phenylloweralkyl, 2-thiophenemethyl, 5-tetrazolylmethyl, $R^3O—$ and $R^3S—$, wherein: $R^3$ stands for lower alkyl, phenyl, phenyllower alkyl;
$R^1$ is hydrogen or a cleavable radical selected from lower alkyl, loweralkoxymethyl, 2,2,2-trichloroethyl, benzyl, p-halobenzyl, p-nitrobenzyl and p-methoxybenzyl, benzhydryl, and trimethylsilyl;
$R^2$ is hydrogen or methoxy;
X is SCl, SBr or —OH (in the latter case, the $C_3$— sidechain is better represented as the amide RCONH— group);
Y is Cl or Br, and

may also be taken as phthalimido.

The novel compounds of the present invention are obtained by methods which are also novel.

These compounds are obtained very conveniently in essentially quantitative yield and high purity by dissolving the unsym-azetidinone disulfides, 16, or the 1,2,4-dithiazineazetidinones, 17, in sulfuryl chloride or sulfuryl bromide (which may be prepared in situ), which function both as reagent and solvent (Flowsheet 4). The reactions are immediate and provide essentially the one isomer depicted, in quantitative yield, the nature and sterochemistry being established by the nmr spectrum of the product in SO$_2$Cl$_2$, or CDCl$_3$, or C$_6$D$_6$ or acetone d$_6$ as solvents.

With the 1,2,4-dithiazineazetidinones, 17, the product is the 3S(α-substituted-α-halosulfenyl)formimino-4S-haloazetidinone-1-α(β-halomethyl-β-halo)butyrate, 18B, (X = SCl or SBr, Y = Cl or Br). These compounds are fairly stable in solution, and solutions in benzene, methylene chloride or chloroform can be washed rapidly with aqueous sodium bicarbonate or water, to remove excess sulfuryl chloride or bromide and acid impurities. The nmr spectra of the washed samples are identical with that of the crude sample. These compounds, 18B, are hydrolysed (stirring with ice water for extended times) to the 3S-substitutedcarbamido-4S-haloazetidinone-1α(β-halomethyl-β-halo)-butylates 18A (Y = Cl or Br). These same compounds, 18A, are also produced by dissolving the unsym-azetidinonedisulfides, 16, in sulfuryl chloride or sulfuryl bromide (which may be prepared in situ). The analysis of 18B (R = φO, X = SCl, Y = Cl, R$^1$ = CH$_3$) indicated the presence of one sulfur and four chlorine atoms in the molecule and the mass spectral analysis agreed with (M-Cl).

Compound 18B (R = φO, X = SCl, Y = Cl, R$^1$ = CH$_3$) with dimethylamine gave methyl 3S-(α-phenoxy-α-dimethylamino) formimino-4S-chloroazetidinone-1-(3'-chloromethylbut-2'-enoate) (cis-isomer), 20A, in excellent yields, the structure being assigned from spectral (nmr, ir, and mass) data. This reaction was specific, giving only the cis-isomer, 20A, none of the isomeric 20B being detectable in the nmr spectrum of the product. Compound 18B, reacted with excess pyridine in benzene to give the dehydrochlorinated azetidinone, 21A, which with dimethylamine formed the isomeric 20B. The nmr spectrum of this compound showed that it was almost entirely one isomer with the geometry indicated, and contained only traces of the isomeric 20A.

Compound 18A (R = φO, R$^1$ = CH$_3$, R$^2$ = H, Y = Cl) underwent a similar reaction with pyridine to give methyl 3S-phenoxyamido-4S-chloroazetidinone-1-(3'-chloromethylbut-2'-enoate) (trans-isomer), 21A. It is hence possible as shown to prepare either of the two isomers 20A and 20B, or 21A by using appropriate conditions.

These compounds show antibacterial activity against *B. subtilis*, *E. Coli* and *Ps. aeruginosa*. In addition they are precursors of intermediates which have been utilised in the preparation of β-lactam antibiotics and their analogues [S. Wolfe and co-workers, *Can. J. Chem.*, 50, 2898, 2902 (1972), and Belgian Pat. No. 832,174, Dec. 1, 1975] to prepare 1-oxacephams.

The present invention will be more readily understood by referring to the following examples which are given to illustrate the invention rather than limit its scope.

EXAMPLE 1

Preparation of 3-Phenoxy-4,5-Dithia-2,7-Diazabicyclo[4,2,0]Oct-2-Ene-8-One-7-Isopropenylacetic Acid 17

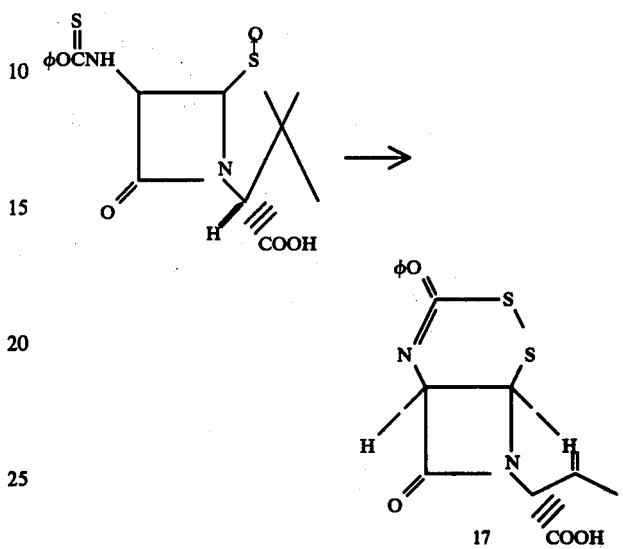

A solution of 6-phenoxythiocarbamidopenicillanic acid sulfoxide (15 g., 0.04 mole) in purified dioxane (300 ml) was heated with stirring under reflux in a dry nitrogen atmosphere in an oil bath maintained at 130°, for 4 hours. The reaction mixture was concentrated in vacuo and dried under hi-vac. The yellowish brown solid thus obtained was dissolved in the minimum amount of warm acetone, the solution treated with charcoal, and filtered. The filtrate was concentrated to about one-third its volume and just sufficient hexane added to induce crystallisation. The mixture was cooled overnight at −10° and the resulting pale yellow crystals isolated by filtration and drying, when 10.5 g (75%) of 3-phenoxy-4,5-dithia-2,7-diazabicyclo[4,2,0]oct-2-ene-8-one-7-isopropenylacetic acid was obtained. The compound could be purified by recrystallisation from acetone-hexane. It was obtained as white crystals, m.p. 146°–148° dec. A high resolution mass spectral analysis gave a mass of 350.0404 for the parent ion, that calculated for C$_{15}$N$_{14}$N$_2$S$_2^{32}$O$_4$ being 350.0396. The nmr (DMSOd$_6$) spectrum: δ7.68-7.15(m, 6H, C$_6$H$_5$ and COO$\underline{H}$), 5.87 and 5.53 (ABq, 2H, J=5Hz, cis-fused β-lactam protons),

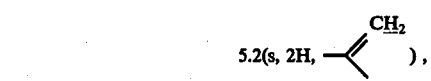

4.85(s, 1H, —C$\underline{H}$COOH),

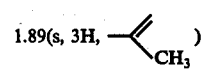

is in agreement with the assignment.

EXAMPLE 2

Preparation of Methyl 3-Phenoxy-4,5-Dithia-2,7-Diazabicyclo[4,2,0]-Oct-2-Ene-8-One-7-Isopropenyl Acetate 17 (ester)

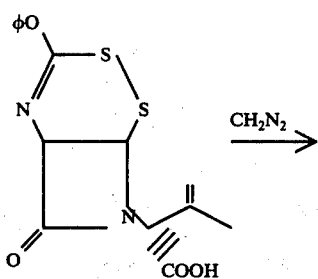

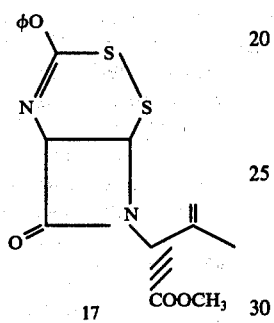

3-Phenoxy-4,5-dithia-2,7-diazabicyclo[4,2,0]oct-2-ene-8-one-7-isopropenylacetic acid (10.0 g., 28.5 mmole) was dissolved in tetrahydrofuran (250 ml) and the solution cooled in an ice-bath. Diazomethane in ether (100 ml -an excess) was added and the solution stirred in the ice-bath for 0.5 hour and then concentrated in vacuo. The residue was taken up in the minimum of ether and cooled in a dry ice-acetone bath while adding an equal volume of hexane. The resulting white precipitate was filtered off and dried to give 7.0 g. of the product. A further 1.5 g. was obtained from the mother liquor after concentration and repeating the ether-hexane precipitation. The two crops were combined (8.5 g., 81%) since they were identical (nmr spectra and tlc). The compound had m.p. 79°–82° C. A high resolution mass spectral analysis gave a measured mass of 364.0565 for the parent ion, while that calculated for $C_{16}H_{16}N_2S_2{}^{32}O_4$ is 364.0552. The nmr (CDCl$_3$) spectrum: $\delta$7.6 to 7.1(m, 5H, C$_6$H$_5$), 5.7 and 5.48(ABq, 2H, J=4Hz, cis-fused $\beta$-lactam protons), 5.22 and 5.12 (d, s, 2H, 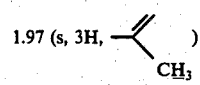), 5.0(s, 1H, CHCOOCH$_3$), 3.8(s, 3H, COOCH$_3$), and 1.97 (s, 3H, —C(=)—CH$_3$)

is in agreement with the assigned structure.

The tlc (ethyl acetate:hexane = 1:2) on silica showed only one compound to be present.

The compound in CDCl$_3$ (unpurified) changes on standing (from the nmr spectrum and the tlc). It is stable in THF solution. In methanol, the reaction with diazomethane gives a mixture of products.

EXAMPLE 3

Methyl 3S-($\alpha$-Phenoxy-$\alpha$-Chlorosulfenyl)Formimino-4S-Chloroazetidinone-1-$\alpha$($\beta$-Chloromethyl-$\beta$-Chloro)Butyrate 18B Methyl 3-phenoxy-4,5-dithia-2,7-diazabicyclo[4,2,0-]oct-2-ene-8-one-7-isopropenyl acetate (0.5 g) was dissolved in purified, distilled sulfuryl chloride (2.5 ml). There was an immediate reaction with production of the title compound as was evident from the nmr spectrum (SO$_2$Cl$_2$) $\delta$7.1(m, 5H, C$_6$H$_5$), 5.25 and 4.77(dd, J=2Hz, 2H, trans-$\beta$-lactam protons), 4.32(s, 1H, CHCOOCH$_3$), 3.79(s, 2H, —CH$_2$Cl), 3.49(s, 3H, COOCH$_3$), 1.4(s, 3H, —CH$_3$). The compound is stable in the SO$_2$Cl$_2$ solution since the nmr spectrum showed no change over a period of 1 hour.

The excess sulfuryl chloride was removed under reduced pressure and the resulting oil dried for about 10 minutes under high vacuum and then dissolved in benzene. The benzene solution was washed rapidly with water (aqueous bicarbonate or bisulfite could also be used), and the organic layer dried over sodium sulfate, filtered and taken to dryness to give a foam. An nmr spectrum (CDCl$_3$ or deuterobenzene) of the residue was the same as for the crude compound (making allowances for the shifts caused by the solvents). The solutions were stable since the nmr samples showed no appreciable change in the spectrum on standing at room temperature for 5 days. The concentrated compound, however, rapidly changed on exposure to air.

The nmr spectrum showed the presence of only the trans-isomer as indicated and no trace of the possible cis-isomer. With regard to the mode of addition of chlorine to the isopropylene double bond, no assignments have been made — a mixture of the erythro-threo isomers may be present.

The compound, although comparatively stable in solution in the absence of air and moisture, changes rapidly on isolation and should be used as quickly as possible. A high resolution mass spectral analysis of the compound gave a measured mass of 436.9890, while that calculated for $C_{16}H_{16}N_2O_4S^{32}Cl_3^{35}$ (M-35) is 436.9898. Elemental analysis showed the presence of sulfur- 6.37% (calc'd for $C_{16}H_{16}N_2SO_4Cl_4$- 6.75; and for $C_{16}H_{16}N_2SO_4Cl_3$-7.3) and chlorine-27.4% (calc'd for $C_{16}H_{16}N_2SO_4Cl_4$ - 30; and for $C_{16}H_{16}N_2SO_4Cl_3$-24.3%) All the evidence would thus support the assigned structure.

Proceeding in the same manner and replacing sulfuryl chloride by sulfuryl bromide prepared 'in situ' provided the methyl 3S- (α-phenoxy-α-bromosulfenyl)formimino-4S-bromoazetidinone-1-α(β-bromomethyl-β-bromo)butyrate.

In a similar manner starting from benzhydryl 3-phenoxy-4,5-dithia-2,7-diazabicyclo[4,2,0]oct-2-ene-8-one-7-isopropenyl acetate,
trichloroethyl 3-phenoxy-4,5-dithia-2,7-diazabicyclo[4,2,0]oct-2-ene-8-one-7-isopropenyl acetate,
benzyl 3-phenoxy-4,5-dithia-2,7-diazabicyclo[4,2,0]oct-2-ene-8-one-7-isopropenyl acetate,
trichloroethyl 3-phenyl-4,5-dithia-2,7-diazabicyclo[4,2,0]oct-2 -ene-8-one-7-isopropenyl acetate, and
trichloroethyl 3-phenoxymethyl-4,5-dithia-2,7-diazabicyclo[4,2,0]-oct-2-ene-8-one-7-isopropenyl acetate the following compounds can be obtained:
benzhydryl 3S-(α-phenoxy-α-chlorosulfenyl)formimino-4S-chloroazetidinone-1-α(β-chloromethyl-β-chloro)butyrate,
trichloroethyl 3S-(α-phenoxy-α-chlorosulfenyl)formimino-4S-chloroazetidinone-1-α(β-chloromethyl-β-chloro)butyrate,
benzyl 3S-(α-phenoxy-α-chlorosulfenyl)formimino-4S-chloroazetidinone-1-α(β-chloromethyl-β-chloro)butyrate, and
trichloroethyl 3-S-(α-phenyl-α-chlorosulfenyl)formimino-4S-chloroazetidinone-1-α(β-chloromethyl-β-chloro)butyrate and
trichloroethyl 3-S-(α-phenoxymethyl-α-chlorosulfenyl)formimino-4S-chloroazetidinone-1-α(β-chloromethyl-β-chloro)butyrate.

EXAMPLE 4

Methyl 3S-Phenoxycarbamido-4S-Chloroazetidinone-1-α(β-Chloromethyl-β-Chloro)-Butyrate 18A

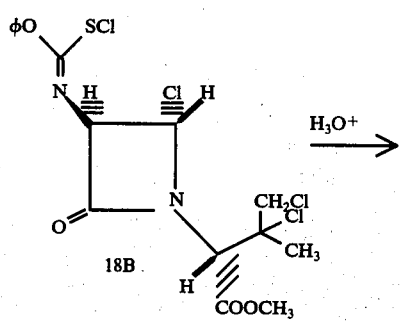

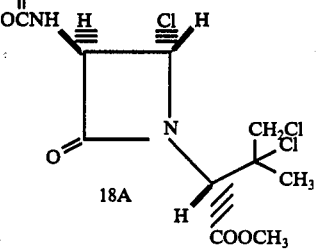

Methyl 3S-(α-phenoxy-α-chlorosulfenyl)formimino-4S-chloroazetidinone-1-α-(β-chloromethyl-β-chloro)-butyrate 18B (73 mg., 0.2 mmole) was dissolved in purified, distilled sulfuryl chloride (1 ml) and the reaction solution concentrated. Ice and water were added to the residue (still containing sulfuryl chloride) with shaking when a white solid (60 mg., after filtration and drying) was obtained. The nmr spectrum ($CDCl_3$) of this sample was identical to that of the title compound made by an alternate route (see Example 8).

Proceeding in the same manner and starting with methyl 3S-(α-phenoxy-α-bromosulfenyl)formimino-4S-bromoazetidinone-1-α(β-bromomethyl-β-bromo)butyrate there is obtained the methyl 3S-phenoxycarbamido-4S-bromoazetidinone-1-α(β-bromomethyl-β-bromo)-butyrate.

EXAMPLE 5

Methyl 3S-(α-Phenoxy-α-Dimethylamino)Formimino-4S-Chloroazetidinone-1-(3'-Chloromethylbut-2'-Enoate) (cis-isomer) 20A

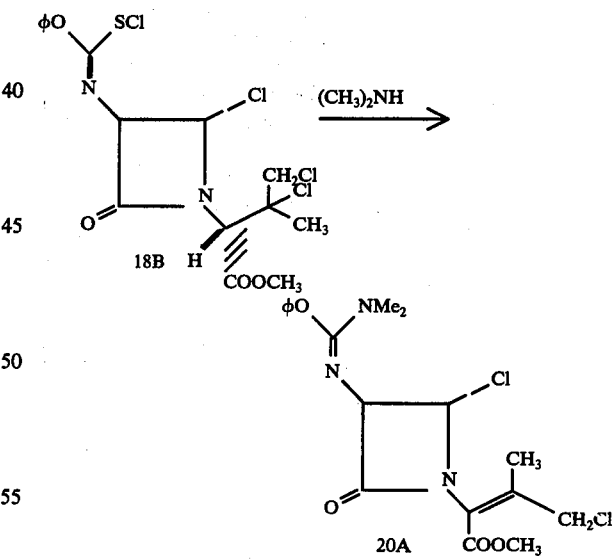

A solution of the methyl ester of the tetrachloro compound, 18B, (3 mmole made as described in Example 3) in dry tetrahydrofuran (25 ml) was cooled to −60° under nitrogen, and dimethylamine (6 mmole) added. The reaction mixture was stirred for 30 mins at −60° and a further 30 mins at −10° and then concentrated. The residue was dissolved in benzene, the resulting solution washed twice with water, dried ($Na_2SO_4$) and concentrated to an oil (1.4 g.). The nmr spectrum indicated that essentially one product was formed. The compound could be purified by precipitation from an ether solution with hexane, or by column chromatography on a silica column using ethyl acetate:hexane (1:1) as eluant. In the latter case, the recovery of the desired compound was only about 25% and this is probably because the compound is labile to the silica. A better method was found to be to filter the compound in ether through a short alumina column and effect further purification by precipitation with hexane from an ether solution. The nmr (CDCl$_3$) spectrum: $\delta$7.67 to 7.0(m, 5H, C$_6$H$_5$), 5.78 and 5.03(dd, J=2Hz, 2H, trans-$\beta$-lactam protons), 4.70(d, J=6Hz, 2H, C$\underline{H}_2$Cl), 3.90(s, 3H, COOC$\underline{H}_3$), 2.98(s, 6H, N(C$\underline{H}_3$)$_2$),

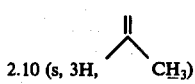

2.10 (s, 3H, CH$_3$)

and mass spectral analysis agreed with the assigned structure. The assignment of geometry of the N-1 substituent is not absolute at this time, however, the nmr spectrum indicates that it is essentially one isomer that is formed in this reaction.

The nmr spectra in C$_6$D$_6$ and acetone d$_6$ were similar except for shifts due to solvent. In acetone d$_6$ the signal assigned the —C$\underline{H}_2$Cl collapsed to a singlet at $\delta$4.2, while in C$_6$D$_6$ a doublet with J=2Hz was obtained at $\delta$3.75. The nmr spectrum taken in conjunction with that of the isomer (Example 6) indicate that the geometry is as indicated [see R. Raap, C. G. Chin and R. G. Micetich, Can.J.Chem., 49, 2143(1971)].

EXAMPLE 6

Methyl 3S-($\alpha$-Phenoxy-$\alpha$-Dimethylamino)Formimino-4S-Chloroazetidinone-1-(3'-Chloromethylbut-2'-Enoate) (trans-isomer) 20B

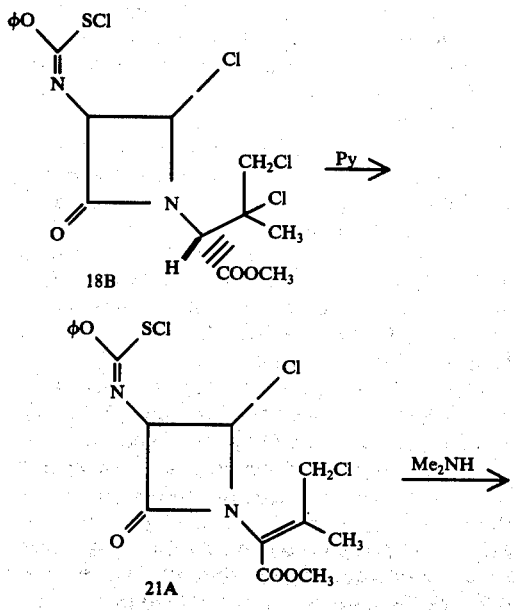

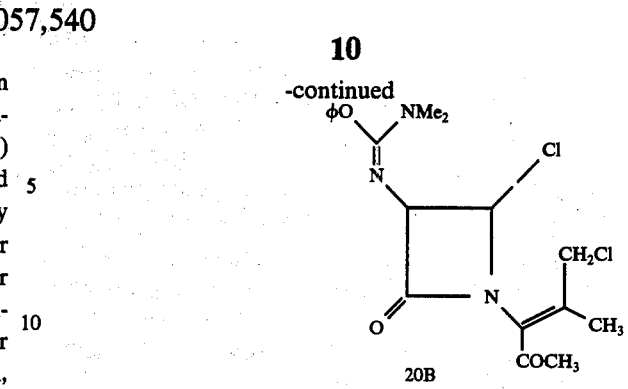

A solution of the methyl ester of the tetrachloro compound, 18B, (made from 364 mg., 1 mmole of the dithiazine azetidinone, 17, by the procedure described before) in benzene (40 ml) was stirred with pyridine (2 ml) at room temperature. [A prior exploratory reaction in which the progress was followed by the nmr spectrum in deuterobenzene with deuteropyridine indicated a reaction time of about 1 hr, the disappearance of the —C$\underline{H}$COOCH$_3$ proton and shifts in the —CH$_2$Cl and

signals being observed]. After 1 hr, the reaction mixture was extracted with hydrochloric acid (0.5 normal), then aqueous bicarbonate and finally water, dried over Na$_2$SO$_4$, filtered and concentrated to give compound 21A as a brown oil. The nmr spectrum was consistent with the assigned structure.

Compound 21A in anhydrous tetrahydrofuran (30 ml) was cooled to $-60°$ and dimethylamine (1.1 mole equivalent) was added. After 20 mins the temperature was raised to $-10°$ and stirred for one hour. The reaction mixture was then concentrated in vaccuo, the residue dissolved in benzene, the benzene solution washed repeatedly with water, dried (Na$_2$SO$_4$) and concentrated to a brown gum whose nmr spectrum (CDCl$_3$) $\delta$7.68 to 7.0 (m, 5H, C$_6$H$_5$), 5.72 and 5.0 (dd, J = 2 Hz, 2H, trans-$\beta$-lactam protons), 4.20 (s, 2H, C$\underline{H}_2$Cl), 3.85 (s, 3H, COOC$\underline{H}_3$), 2.99 (s, 6H, N(CH$_3$)$_2$), 2.33 (s, 3H, =C—C$\underline{H}_3$) is consistent with the assigned structure and shows that essentially one isomer (of opposite geometry from that in Example 5) is formed.

EXAMPLE 7

Methyl 2-Oxo-3-(Phenoxyamido)-4-(benzothiazol-2-yl)Dithio-$\alpha$-Isopropenyl-azetidin-1-Acetate, 16

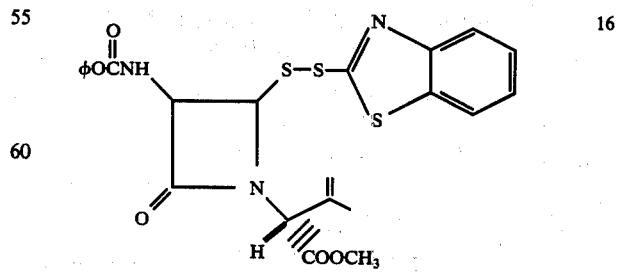

A solution of methyl 6-phenoxyamidopenicillanate sulfoxide (11.0 g., 30 mmoles) and 2-mercaptobenzothiazole (5.5 g., 33 mmoles) in dioxane (180 ml) was heated under reflux for 6 hrs. Concentration gave a residue (16.1 g.), a portion (13.6 g.) of which was chromatographed on Mallinckrodt Silicar CC-7 (300 g., 200-325 mesh) using benzene-ethyl acetate mixtures. Elution with 4:1 and 3:2 benzene-ethyl acetate mixtures gave the title compound (9 g.) of sufficient purity for further transformations. The compound had an ir spectrum (CHCl$_3$): 1780 and 1750 cm$^{-1}$; nmr spectrum (CDCl$_3$): δ1.90(s, 3H), 3.73(s, 3H), 4.93(s, 1H), 5.07(br,s, 1H), 5.20(br,s,1H), 5.40(q, J = 5 and 8Hz, 1H), 5.58(d, J = 5Hz, 1H) and 6.9 to 8.1(m.).

EXAMPLE 8

Methyl 3S-Phenoxyamido-4S-Chloroazetidinone-1-α(β-Chloromethyl-β-Chloro-Butyrate 18A

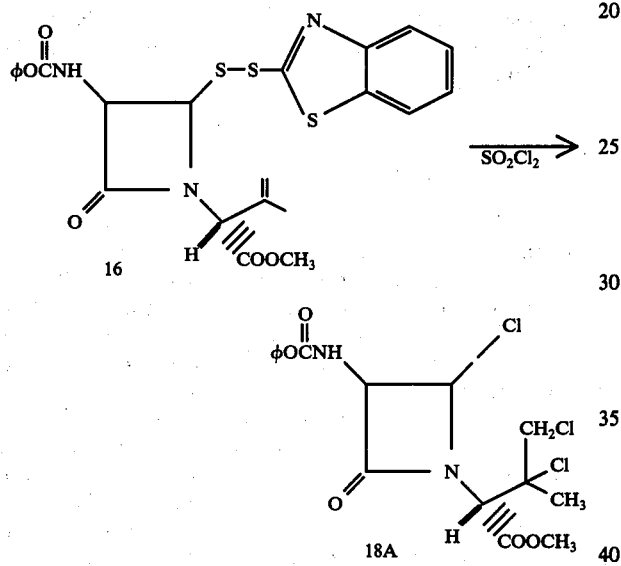

Methyl 2-oxo-3-(phenoxyamido)-4-(benzothiazol-2-yl)dithio-α-isopropenylazetidin-1-acetate (70 mg) was stirred with purified distilled sulfuryl chloride (1 ml). Thee was an immediate reaction, the compound dissolved to a yellow solution and very quickly a yellow solid (probably benzothiazoledisulfide) separated. This solid slowly redissolved (probably due to formation of the benzothiazolesulfenyl chloride - the other product in this reaction). The solution was concentrated, and redissolved in CDCl$_3$. The nmr spectrum of this solution: δ8.35 to 7.15(m, C$_6$H$_5$ and benzothiazole protons), 6.45(d, J = 7Hz, —NH—), 5.9(d, J = 2Hz, azetidinone C$_4$-H), 5.0(dd, azetidinone C$_3$-H), 4.8(s, CHCOOCH$_3$), 4.19(s, CH$_2$Cl), 3.85(s, COOCH$_3$),

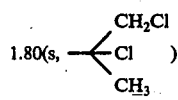 1.80(s, is in agreement with the assigned structure. The nmr spectrum again showed only one isomer (trans-β-lactam protons from the J value) to be present). The N-1 substituent could of course consist of the erythro-threo isomers.

EXAMPLE 9

Methyl 3S-Phenoxyacetamido-4S-Chloroazetidinone-1-α-(β-Chloromethyl-β-Chloro)Butyrate 18A

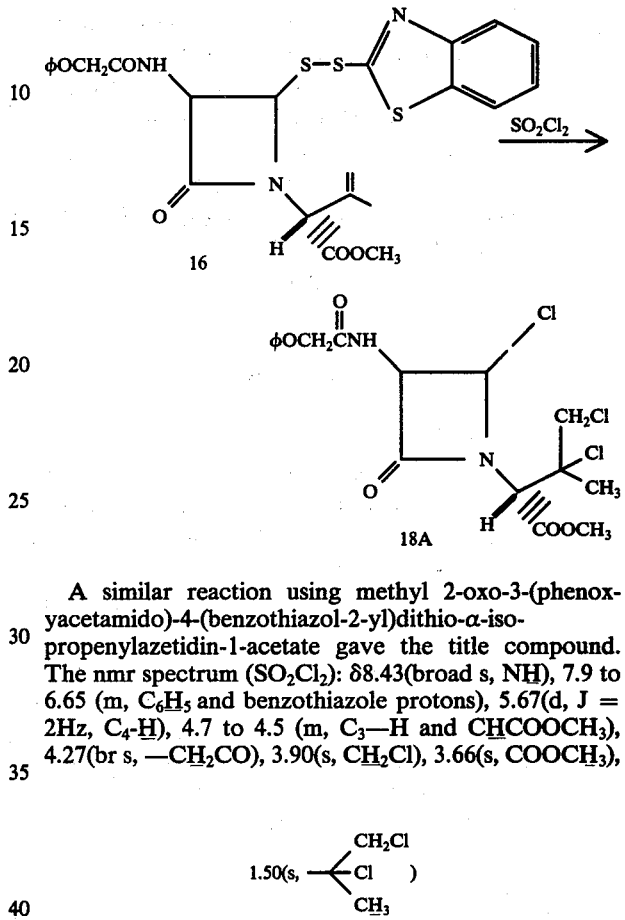

A similar reaction using methyl 2-oxo-3-(phenoxyacetamido)-4-(benzothiazol-2-yl)dithio-α-isopropenylazetidin-1-acetate gave the title compound. The nmr spectrum (SO$_2$Cl$_2$): δ8.43(broad s, NH), 7.9 to 6.65 (m, C$_6$H$_5$ and benzothiazole protons), 5.67(d, J = 2Hz, C$_4$-H), 4.7 to 4.5 (m, C$_3$—H and CHCOOCH$_3$), 4.27(br s, —CH$_2$CO), 3.90(s, CH$_2$Cl), 3.66(s, COOCH$_3$),

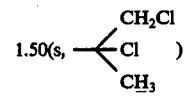 1.50(s, was also clear and showed only one azetidinone C$_4$-isomer trans-β-lactam protons from the J value) to be present.

Proceeding in the same manner and using sulfuryl bromide formed 'in situ' instead of sulfuryl chloride there is obtained the methyl 3S-phenoxyacetamido-4S-bromoazetidinone-1-α(β-bromomethyl-β-bromo)butyrate.

In a similar manner using:
trichloroethyl 2-oxo-3-(phenoxyamido)-4-(benzothiazol-2-y)dithio-α-isopropenylazetidin-1-acetate,
benzyl 2-oxo-3-(phenoxyamido)-4-(benzoxazol-2-yl)dithio-α-isopropenylazetidin-1-acetate,
trichloroethyl 2-oxo-3-(phenoxyacetamido)-4-(benzothiazol-2-yl)dithio-α-isopropenylazetidin-1-acetate,
benzyl 2-oxo-3-(phenoxyacetamido)-4-(benzoxazol-2-y)dithio-α-isopropenylazetidin-1-acetate,
trimethylsilyl 2-oxo-3-(phenoxyacetamido)-4-(benzothiazol-2-yl)dithio-α-isopropenylazetidin-1-acetate,
trichloroethyl 2-oxo-3-(phenylacetamido)-4-(benzothiazol-2-yl)dithio-α-isopropenylazetidin-1-acetate,
benzyl 2-oxo-3-(phenylacetamido)-4-(benzothiazol-2-yl)dithio-α-isopropenylazetidin-1-acetate,
trimethylsilyl 2-oxo-3-(phenylacetamido)-4-(benzothiazol-2-y)dithio-α-isopropenylazetidin-1-acetate,
trichloroethyl 2-oxo-3-(benzamido)-4-(benzothiazol-2-yl)dithio-α-isopropenylazetidin-1-acetate, trichloroethyl 2-oxo-3-(thien-2'-ylactamido)-4-(benzothiazol-2-yl)dithio-α-isopropenylazetidin-1-acetate, and trichloroethyl 2-oxo-3-methoxy-3-phenoxyacetamido-4-(benzothiazol-2-yl)dithio-α-isopropenylazetidin-1-acetate it is possible to prepare:

trichloroethyl 3S-phenoxyamido-4S-chloroazetidinone-1-α(β-chloromethyl-β-chloro)butyrate, benzyl 3S-phenoxyamido-4S-chloroazetidinone-1-α(β-chloromethyl-β-chloro)butyrate, trichloroethyl 3S-phenoxyacetamido-4S-chloroazetidinone-1-α(β-chloromethyl-β-chloro)butyrate, benzyl 3S-phenoxyacetamido-4S-chloroazetidinone-1-α(β-chloromethyl-β-chloro)butyrate, trimethylsilyl 3S-phenoxyacetamido-4S-chloroazetidinone-1-α(β-chloromethyl-β-chloro)butyrate, trichloroethyl 3S-phenylacetamido-4S-chloroazetidinone-1-α(β-chloromethyl-β-chloro)butyrate, benzyl 3S-phenylacetamido-4S-chloroazetidinone-1-α(β-chloromethyl-β-chloro)butyrate, trimethylsilyl 3S-phenylacetamido-4S-chloroazetidinone-1-α(β-chloromethyl-β-chloro)butyrate, trichloroethyl 3S-benzamido-4S-chloroazetidinone-1-α(β-chloromethyl-β-chloro)butyrate, trichloroethyl 3S-(thien-2'-ylacetamido)-4S-chloroazetidinone-1-α(β-chloromethyl-β-chloro)butyrate, and trichloroethyl 3-methoxy-3S-(phenoxyacetamido)-4S-chloroazetidinone-1-α(β-chloromethyl-β-chloro)butyrate.

EXAMPLE 10

Methyl 3S-Phenoxyacetamido-4S-Chloroazetidinone-1-(3'-Chloromethylbut-2'-enoate) (trans-isomer) 21A

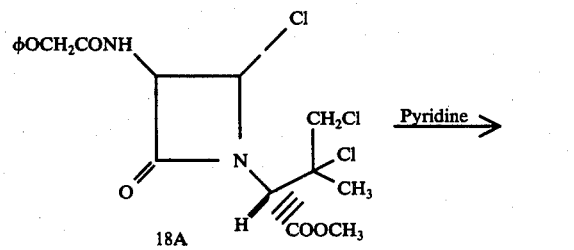

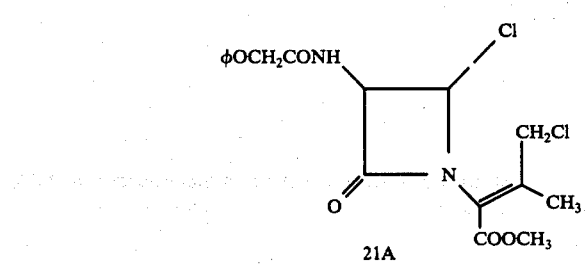

Methyl 3S-phenoxyacetamido-4S-chloroazetidinone-1-α(β-chloromethyl-β-chloro)butyrate, 18A (2 g., 4.78 mmoles) was dissolved in pyridine (10 ml) in an ice bath. After 5 minutes most of the pyridine was removed in vaccuo at about 30° and the residue dissolved in benzene. The benzene solution was washed with hydrochloric acid (1N), saturated aqueous sodium bicarbonate, and water and then dried (Na$_2$SO$_4$). The residue after filtration and concentration was dissolved in the minimum of ether. Addition of hexane precipitated a yellowish solid (1.05 g., about 60%) whose nmr spectrum (CDCl$_3$) δ2.32 (s, 3H, =C—C$\underline{H}$$_3$), 3.80 (s, 3H, COOC$\underline{H}$$_3$), 4.30 (d, J = 8 c/s, 2H, =C—C$\underline{H}$$_2$Cl), 4.50 (s, 2H, OC$\underline{H}$$_2$CO), 5.00 (dd, 1H, C$_3$—$\underline{H}$), 6.05 (d, J = 2 c/s, 1H, C$_4$—$\underline{H}$), 6.8 to 7.65 (m, 5H, C$_6$$\underline{H}$$_5$) is characteristic of 21A. The assignment of the trans-stereochemistry is provisional and made by comparison of the nmr spectra with those of compounds 20A and 20B.

EXAMPLE 11

Methyl 3S-Phenoxyamido-4S-Chloroazetidinone-1-(3'-Chloromethylbut-2'-enoate) (trans-isomer) 21A

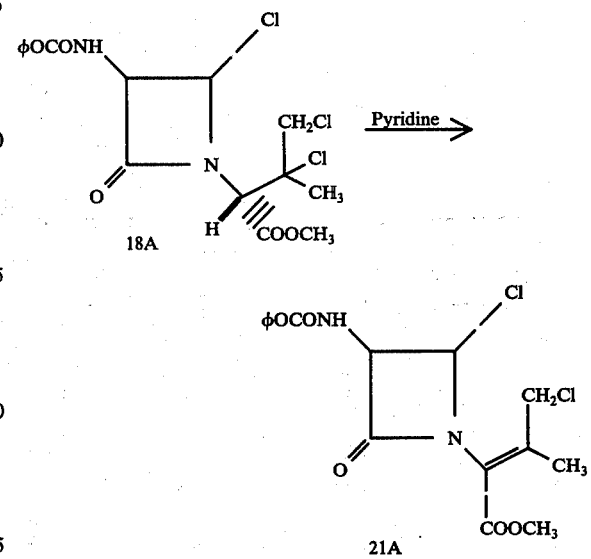

Methyl 3S-phenoxyacetamido-4S-chloroazetidinone-1-α(β-chloromethyl-β-chlorobutyrate), 18A (4.5 g) was dissolved in pyridine (20 mls) in an ice bath. The pyridine was removed (under vacuum) immediately after solution of 18A was complete, using benzene as a chaser (approximate time 25 mins). The resulting brown gum was dissolved in benzene and the resulting solution washed with hydrochloric acid (1 normal), then aqueous sodium bicarbonate, then water, and the benzene solution then dried (MgSO$_4$). The residue after filtration and concentration was taken up in ether and precipitated with hexane (at −60° C) to give 2.3 g., (estimated 61%) of a pale white powder. The nmr spectrum (CDCl$_3$), δ2.32 (s, 3H, =C—C$\underline{H}$$_3$), 3.80 (s, 3H, COOC$\underline{H}$$_3$), 4.20 (d, 2H, =C—C$\underline{H}$$_2$Cl), 4.90 (dd, 1H, C$_3$—$\underline{H}$), 6.0 (d, J = 2 c/s. 1H, C$_4$—$\underline{H}$), 6.32 (d, 1H, N$\underline{H}$), 7.15 to 7.40 (m, 5H, C$_6$$\underline{H}$$_5$) is in agreement with the assigned structure.

FLOWSHEET 1
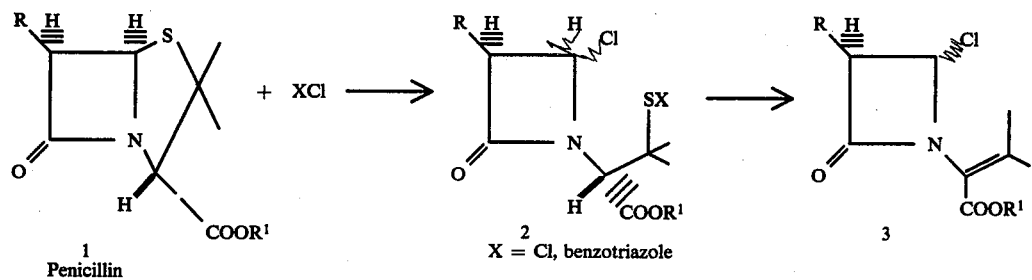
1
Penicillin
2
X = Cl, benzotriazole
3
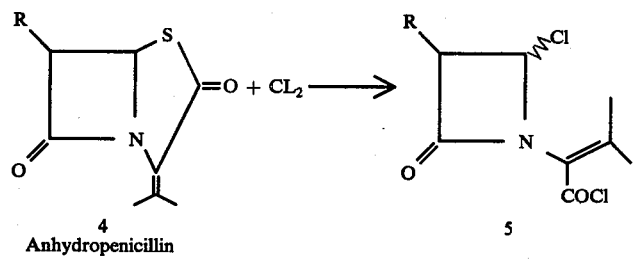
4
Anhydropenicillin
5
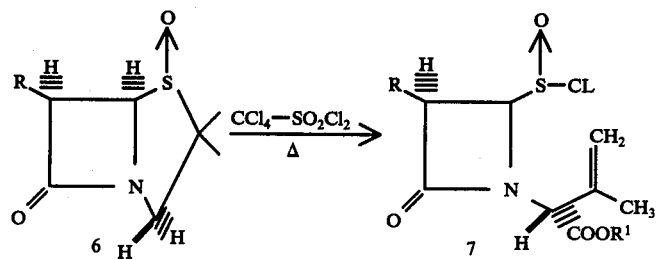
6
7
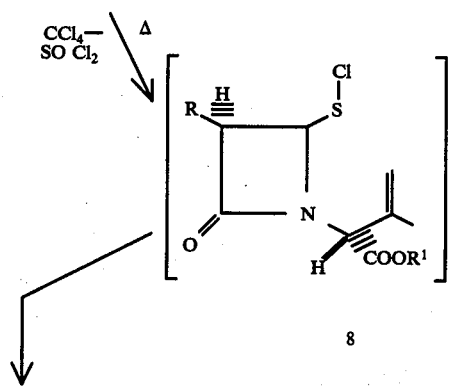
8

-continued
FLOWSHEET 1
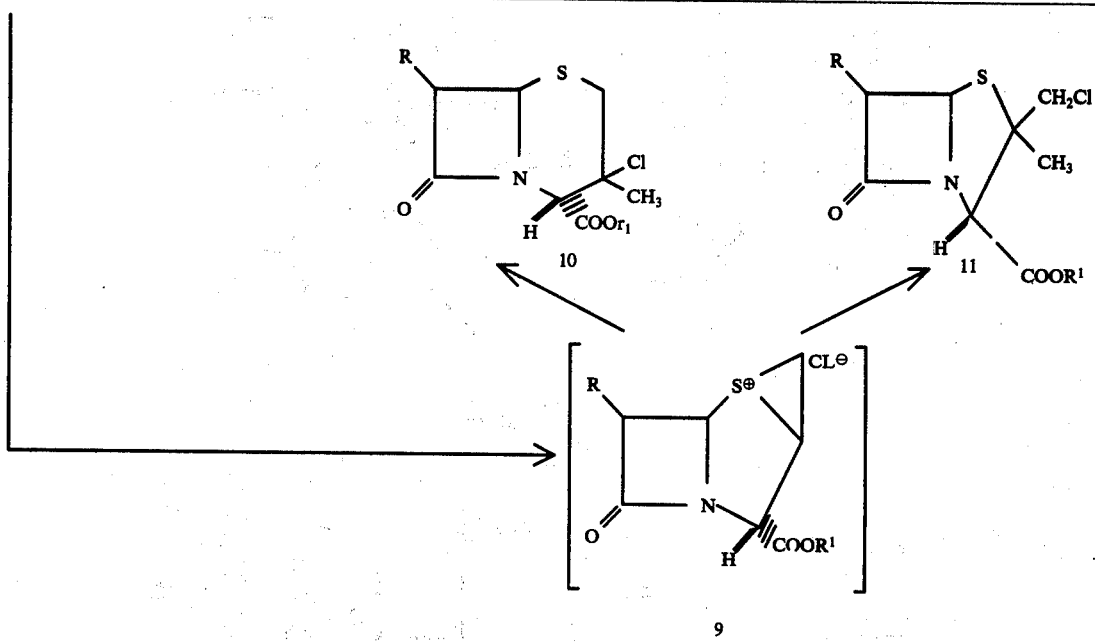
FLOWSHEET 2
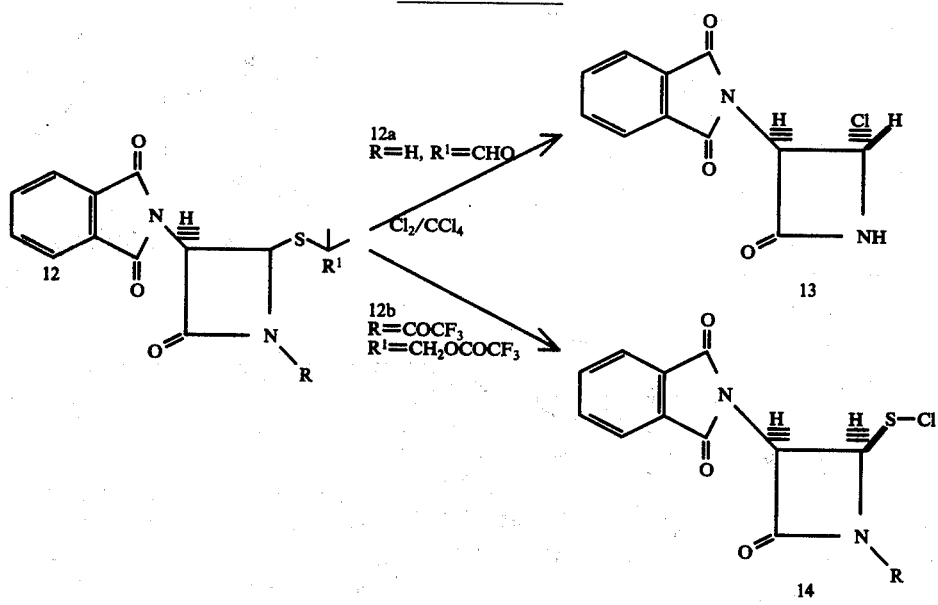
FLOWSHEET 3
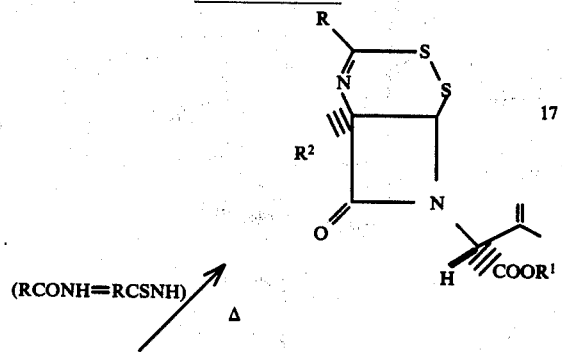

FLOWSHEET 3
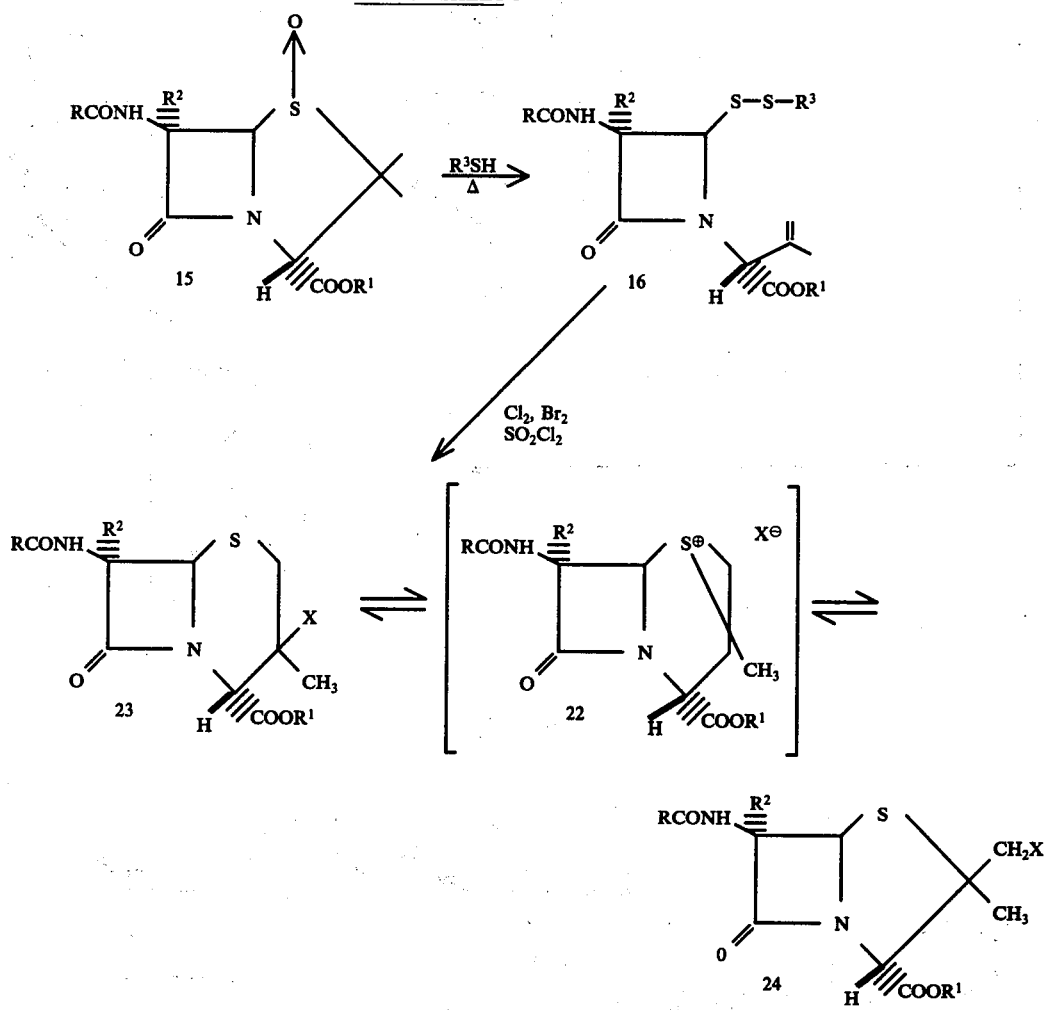
FLOWSHEET 4
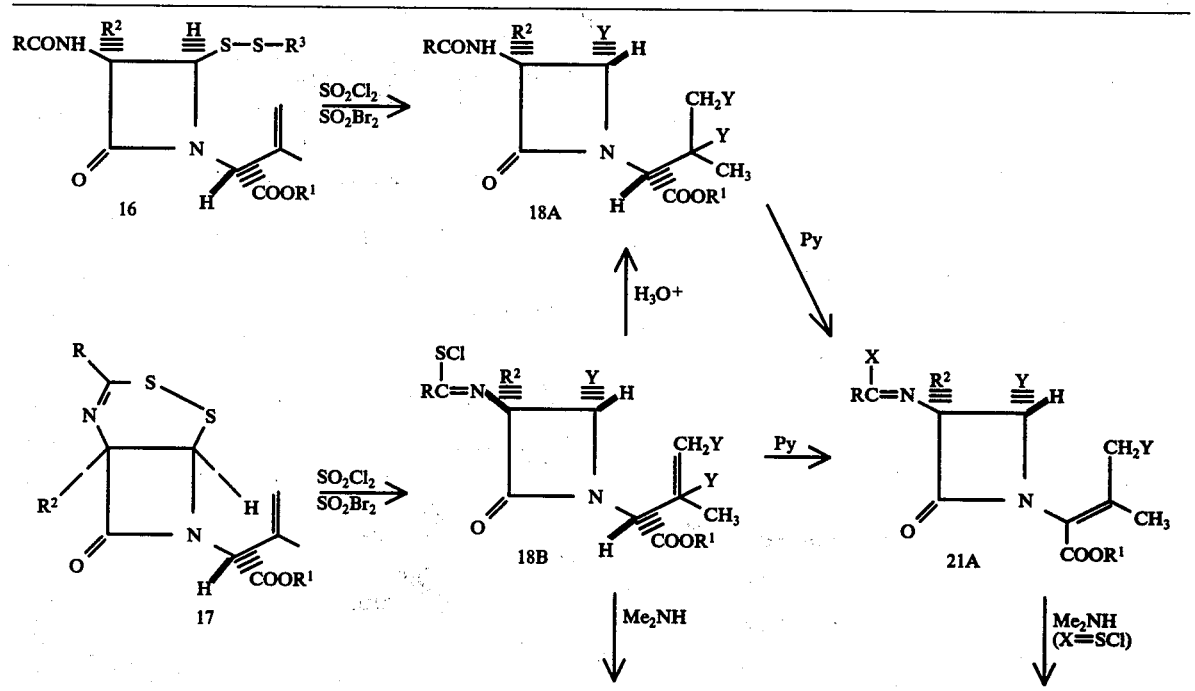

-continued
FLOWSHEET 4

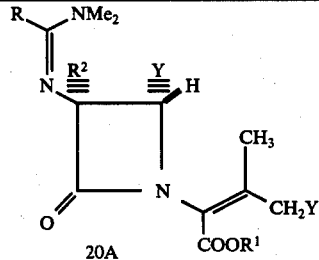

20A

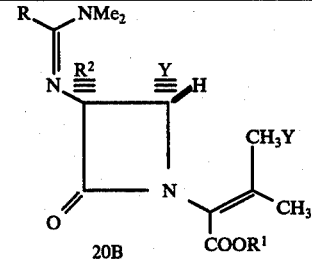

20B

What is claimed is:
1. A compound of the general formula:

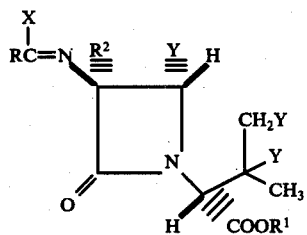

wherein:
R stands for lower alkyl, phenyl, phenyloxyloweralkyl, phenylloweralkyl, 2-thiophenemethyl, 5-tetrazolylmethyl, $R^3O—$ and $R^3S—$, wherein: $R^3$ stands for lower alkyl, phenyl or phenylloweralkyl;
$R^1$ is hydrogen or a cleavable radical selected from lower alkyl, loweralkoxymethyl, 2,2,2-trichloroethyl, benzyl, p-halobenzyl, p-nitrobenzyl and p-methoxybenzyl, benzhydryl and trimethylsilyl;
$R^2$ is hydrogen;

is RCONH or phthalimido
Y is chloro or bromo.
2. The compound of claim 1 wherein R is phenoxy and

is RCONH.
3. The compound of claim 1 wherein R is phenoxymethyl and

is RCONH.
4. The methyl 3S-phenoxycarbamido-4S-chloroazetidinone-1-α(β-chloromethyl-β-chloro)butyrate.
5. The methyl 3S-phenoxyacetamido-4S-chloroazetidinone-1-α(β-chloromethyl-β-chloro)butyrate.

* * * * *